United States Patent [19]

Hannah et al.

[11] Patent Number: 4,695,565
[45] Date of Patent: Sep. 22, 1987

[54] ANTIBACTERIAL 7β-HETEROCYCLIC-CEPHEM

[75] Inventors: John Hannah, Matawan; Burton G. Christensen, Cliffside, both of N.J.

[73] Assignee: Merck & Co., Inc., Rahway, N.J.

[21] Appl. No.: 679,413

[22] Filed: Dec. 7, 1984

Related U.S. Application Data

[63] Continuation-in-part of Ser. No. 657,711, Oct. 4, 1984, abandoned.

[51] Int. Cl.$^4$ .................. C07D 501/18; A61K 31/545
[52] U.S. Cl. .................................... 514/206; 540/227
[58] Field of Search .................... 544/27; 548/213; 540/227; 514/206

[56] References Cited

U.S. PATENT DOCUMENTS

| | | | |
|---|---|---|---|
| 4,255,424 | 3/1981 | Hannah | 424/248.51 |
| 4,283,397 | 8/1981 | Hannah | 424/246 |
| 4,327,210 | 4/1982 | Montavon et al. | 544/27 |
| 4,348,518 | 9/1982 | Montavon et al. | 544/27 |
| 4,358,447 | 4/1979 | Hannah | 424/246 |
| 4,412,070 | 10/1983 | Reiner et al. | 544/27 |
| 4,474,779 | 10/1984 | Nagano et al. | 548/213 |

OTHER PUBLICATIONS

Nagano et al., "Cephalosporin Compounds", *Chem. Abst.* 98:89072u (1983).

Dunn, G. L., "Ceftizoxime and Other Third-generation Cephalosporins", *J. Antimicrob. Chem.* (1982) 10 Supp. C, 1–10.

John Hannah, et al.—"Quaternary Heterocyclylamino β-Lactams: A Generic Alternative to the Classical Acylamino Side Chain", J. Med. Chem. 1982, 25, 457–469.

*Primary Examiner*—Donald G. Daus
*Assistant Examiner*—William A. Teoli, Jr.
*Attorney, Agent, or Firm*—Raymond M. Speer; Hesna J. Pfeiffer

[57] ABSTRACT

This application discloses antibacterial cephems of the formula:

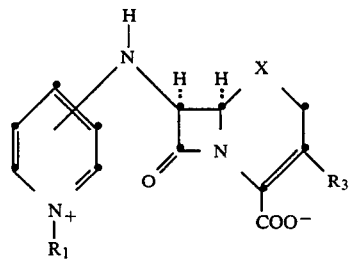

wherein $R_1$ represents hydrogen, alkyl, alkenyl, heterocyclylalkyl, or aralkyl; $R_3$ is a 5- or 6-membered heterocyclic ring selected from:

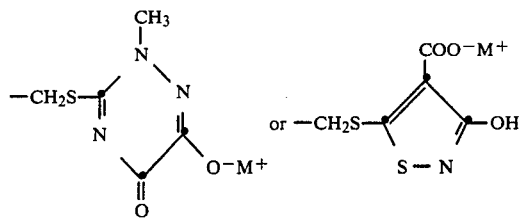

and X is sulfur or oxygen.

Included also are pharmaceutically acceptable salts and esters of such compounds; pharmaceutical compositions thereof, and methods of treatment comprising such compositions when an antibiotic effect is needed.

4 Claims, No Drawings

ANTIBACTERIAL 7β-HETEROCYCLIC-CEPHEM

REFERENCE TO RELATED APPLICATIONS

This application is a continuation-in-part of application Ser. No. 657,711, filed Oct. 4, 1984, now abandoned.

BACKGROUND OF THE INVENTION

This invention relates to a new class of cephalosporins and their pharmaceutically acceptable salts and esters which are useful as long-acting antibiotics. This new class of cephalosporins are represented by formula I:

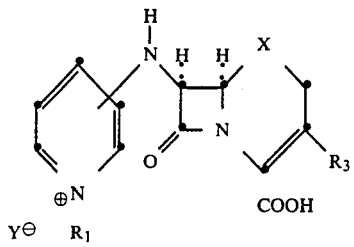

I wherein $R_1$, $R_3$ and X are as defined above, and the pyridine ring is connected to the amino nitrogen at the 2 or 4 position and wherein Y is a pharmaceutically acceptable anion such as chloride, sulfate, acetate, propionate, citrate, tartrate or the like.

Isolation from basic solution (aqueous for example) yields salts which may be represented by the following structures:

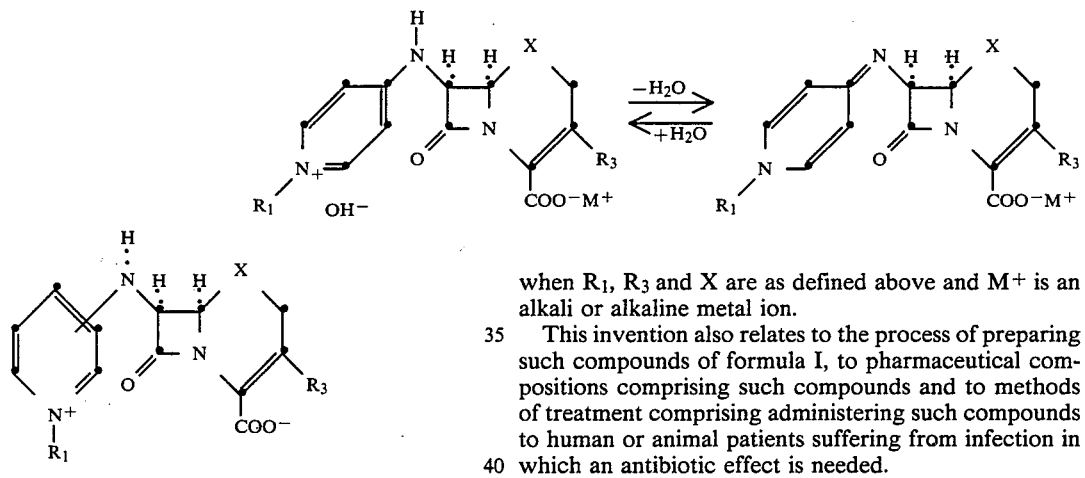

when $R_1$, $R_3$ and X are as defined above and $M^+$ is an alkali or alkaline metal ion.

This invention also relates to the process of preparing such compounds of formula I, to pharmaceutical compositions comprising such compounds and to methods of treatment comprising administering such compounds to human or animal patients suffering from infection in which an antibiotic effect is needed.

There is a continuing need for new antibiotics. In particular, there is a need for cephalosporin type antibiotics which have the similar antibacterial spectrum but which have a longer lasting effect when a therapeutic dose is administered. Many of the cephalosporin antibiotics are known to be eliminated relatively rapidly from the bloodstream following adminstration, thus requiring frequent administration of medication to maintain an effective blood level of antibiotic.

Thus, it is an object of the present invention to provide a novel class of antibiotics which are useful in animal and human therapy and in inanimate systems. These antibiotics are active against a broad range of pathogens which representatively include both gram-positive bacteria such as *S. aureus*, *Strep. pyogenes*, and *B. subtilis*, and gram-negative bacteria such as *E. coli*, Pseudomonas, *Proteus marganii*, Serratia, and Klebsiella. Further objects of this invention are to provide chemical processes for the preparation of such antibiotics and their non-toxic pharmaceutically acceptable salts and esters; pharmaceutical compositions comprising such antibiotics; and to provide methods of treatment comprising administering such antibiotics and compositions when an antibiotic effect is indicated. It is a still further object to provide cephalosporin analogs which are retained for longer periods of time in the patient being treated than is ordinarily true of presently known cephalosporins.

wherein the pyridine ring is connected to the amino nitrogen at the 2 or 4 position of the pyridine ring. and wherein:

$R_1$ is a hydrogen, substituted or unsubstituted alkyl, alkenyl, heterocyclylalkyl, or aralkyl, $R_3$ is a 5- or 6-membered heterocyclic thio methyl substituent selected from groups of the formula:

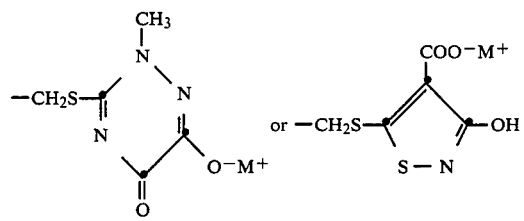

wherein $M^+$ is an alkali or alkaline earth metallic cation such as $Na^+$ and $K^+$, and X is S or O.

The compounds of the present invention are most conveniently isolated as the zwitterionic species described by Formula I hereinabove. This structure is the principal one, however other forms can be preferred using alternate isolation procedures. Isolation from acidic solution provides salts which may be represented by the following structure:

DETAILED DESCRIPTION OF THE INVENTION

The compounds of the present invention are prepared by reacting an appropriately substituted 7-aminocephalosporin (1) or 7-aminooxadethiacephalosporin with a chosen electrophilic substituted pyridine (2) calculated to produce the species of the invention I. The following reaction diagram illustrates the process indicating the structure of the reagents used and the major product produced (I, above).

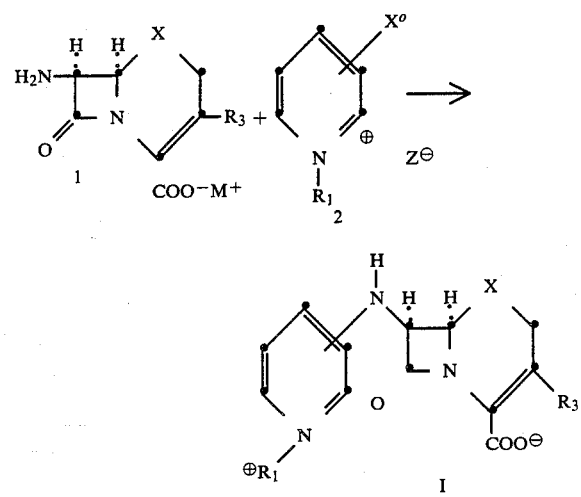

wherein:

R₃ is a 5- or 6-membered heterocyclic thio methyl substituent selected from halide.

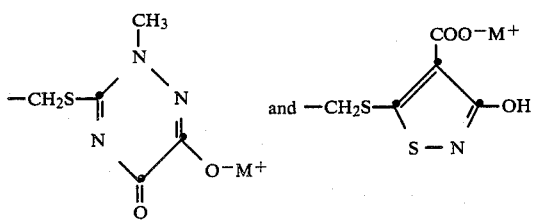

$M^+$ is a cation selected from alkali or alkaline earth metal such as $Na^+$ and $K^+$;

X is S or O; and

Z is an anion selected from halide.

$R_1$ is selected from H, substituted and unsubstituted alkyl having 1-10 carbon atoms, alkenyl having 2-10 carbon atoms, phenylalkyl, phenyl alkenyl having 7-12 carbon atoms, X° is a leaving group including halogen, preferably fluorine, also $OCH_3$, $SCH_3$, $OSO_2OCH_3$, $OSO_2OCF_3$.

In carrying out the reaction the selected 7-aminoceph-3-em-4-carboxylic acid or 7-aminooxadethiaceph-3-em-4-carboxylic acid is suspended in water and dissolved by stirring in sufficient 2.5N sodium hydroxide solution to bring the pH to 7.0. To the vigorously stirred solution is then added an aqueous solution of the heterocyclic reagent and additional aqueous sodium hydroxide is added to maintain the pH at 6.5–7.0 until the reaction is substantially complete in a period of from 15 minutes to 2 hours. Acidification of the reaction solution to pH 3.5 in the case of insoluble products, precipitates the product in crude form.

A convenient method of isolating the product in substantially pure form is by the use of reverse phase HPLC using (ODS) octadecyl silane bonded to silica and using a UV detector and aqueous tetrahydrofuran (1–30%) as the mobile phase. Fractions selected by UV are combined and lyophilized to produce pure product.

The antibiotics of the present invention I are valuable antibiotics active against various gram-positive and gram-negative bacteria and accordingly find utility in human and veterinary medicine. Representative pathogens which are sensitive to antibiotics I include: *Staphylococcus aureus, Escherichia coli, Klebsiella pneumoniae, Bacillus subtilis, Salmonella typhosa,* Pseudomonas and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, any be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycine; lubricants, for example, magnesium stearate, talc, polyethylene glycol, silica; disintegrants, for example, potato starch; or acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution, at the time of delivery, with a suitable vehicle, such sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be present in liquid or semisolid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to % of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure zwitterionic compound in sterile water solution or in the form of a soluble powder intended for solution. The pH of such solutions typically will correspond to the zwitterionic point; however, consideration of individual properties of solubility and stability may require such aqueous solutions to have a pH other than that of the zwitterionic point, for example in the range of 5.5 to 8.2.

The following examples, illustrate but do not limit the product, process, compositional or method of treatment aspects of the present invention. All reaction temperatures are in °C.

PREPARATION 1

3-Acetoxymethyl-7β-amino-1-oxa-1-dethiaceph-3-em-4-oic Acid

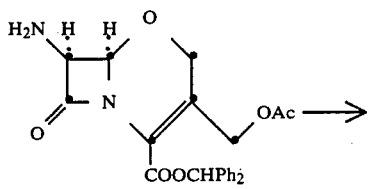

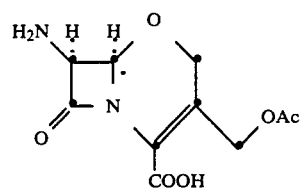

3-Acetoxymethyl-7β-amino-1-oxa-1-dethiaceph-3-em-4-oic acid benzhydryl ester* (1 g) is dissolved/suspended in anisole (10 ml) at 0°, and trifluoroacetic acid (30 ml) is added dropwise with stirring. A clear solution is formed which is left at 0° for 1 hour and is then evaporated at 0°/0.1 mm. The residue is partitioned between water and methylene chloride. The aqueous acidic layer is separated and the pH is adjusted to 3.5 by adding aqueous N NaOH. The product precipitates and is filtered off; washed with water; dried at 30°/0.1 mm; and obtained as a pale tan powder.

*Preparation described in M. Narisada et al., J. Med. Chem. 22, 757, (1979).

EXAMPLE 1

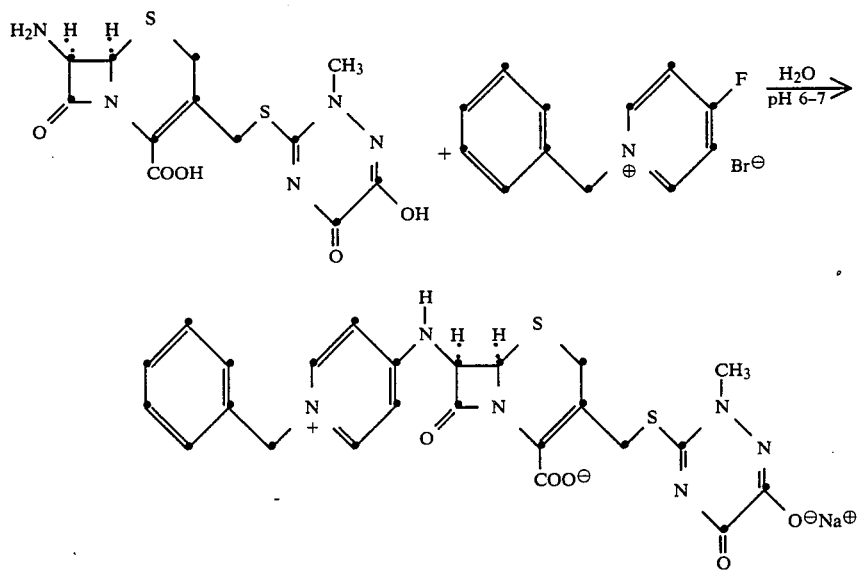

Aqueous 2.5N NaOH was added slowly from a hypodermic to a vigorously stirred suspension of 7β-amino-3-[{(2,5-dihydro-6-hydroxy-2-methyl-5-oxo-1,2,4-triazin-3-yl)thio}methyl]ceph-3-em-4-oic acid[1] in water (5 ml) [pH was about 4.5] at 25° at a rate not exceeding pH 7 in the mixture. The compound was readily soluble.

[1] European patent 0065748 publisehd 18 May 1982 R. P. Hug Hoffman-La Roche

The mixture was filtered from traces of insolubles; and to the clear dark red filtrate was added solid 1-benzyl-4-fluoropyridinium bromide (83% reagent), which dissolved instantly, lowering the pH to about 5.

Aqueous 2.5N NaOH was again added to the vigorously stirred solution at a rate not exceeding pH 6.5. 0.32 ml was added in 10 minutes; thereafter the rate was much slower, with a total of 0.48 ml added in 30 minutes to a pH of 7.0.

The clear red solution was the acidified slowly dropwise with aqueous N HCl to pH 3.5 with very vigorous stirring. A voluminous brown precipitate was formed, somewhat gummy at first, then becoming more granular.

The mixture was filtered; the solids were washed with water (2×2 ml); with acetone (2×5 ml); dried at 50°/0.5 mm; and obtained as a pale brown powder (637 mg), [A]. DMSO NMR-XL200—correct product contaminated with 1-benzylpyridone. This product was re-dissolved in water (6.4 ml) by adding an equivalent of NaHCO$_3$ (99 mg). Half of the solution was injected into a reverse-phase HPLC system using a Whatman Partisil M20 10/50 ODS.3. column with aq. 2% THF as the mobile phase, pumped at 9.9 ml/min. Pure product (monitored by U.V.) was collected at 33–52 minutes. The process was repeated with the remainder of the crude solution.

The combined product eluate was lyophylized to yield the quaternary carboxylate sodium salt as a colorless powder (265 mg) (35%). UV (H$_2$O) max 282 mm (45,000); NMR (D$_2$O) (XL 200) 3.39, 3.48, 3.66, 3.75 (ABq, 2H, J=18.3 Hz, C$_2$—H); 3.60 (s, 3H, CH$_3$—N triazine); 4.03, 4.09, 4.31, 4.38 (ABq, 2H, J=13.5 Hz, C$_3$—CH$_2$S—); 5.27 (d, 1H, J=4.3 Hz, H$_6$); 5.42 (S, 2H, N$^+$CH$_2$); (5.65 (d, 1H, J=4.3 Hz, H$_7$); 7.05 (d, 2H, J=6.8 Hz, H$_{3'}$+H$_{5'}$); 8.40–8.54 (m, 5H, Ar) 8.25 (broad s, 2H, H$_{2'}$+H$_{6'}$).

EXAMPLE 2

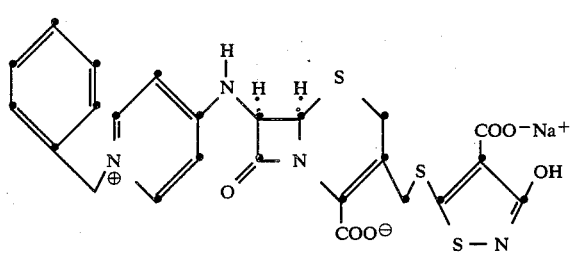

The procedure of Example 1 is repeated using 7β-amino-3-[(3-hydroxy-4-carboxy-isothiazol-5-yl)-[{(3-thio}methyl]ceph-3-em-4-oic acid[2] as the cephalosporin reactant and 1-benzyl-4-fluoropyridinium bromide as the heterocyclic reactant.

[2] Japanese Kohai 58/157792 published 19 Sept. 1983

EXAMPLE 3

7β-Amino-3-[(2,5-dihydro-6-hydroxy-2-methyl-5-oxo-1,2,4-triazin-3-yl)thio methyl]-1-oxa-1-dethiaceph-3-em-4-oic Acid

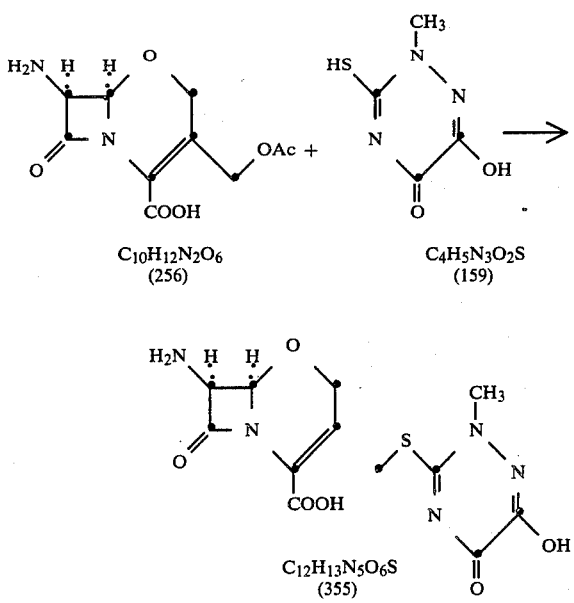

Sodium bicarbonate (3.25 mol) is added to a suspension of 3-acetoxymethyl 7β-aminooxadethiacephalosporanic acid (7.0 g, 1 mol) in water (210 ml) at 25° forming a clear solution to which 2,5-dihydro-6-hydroxy-3-mercapto-2-methyl-5-oxo-1,2,4-trioxime (5.1 g, 1.25 mol) is added. The solution is then heated to 50° under nitrogen with stirring for 15 hours. The solution is cooled to 20° and slowly acidified with aqueous 2N HCl to pH=3.5, which precipitates the desired product. The solids are filtered off; washed with water (2×25 ml); with acetone (2×25 ml); dried at 50°/0.5 mm; and are obtained as a pale tan powder (4.0 g).

EXAMPLE 4

7β-Amino-3-[(4-carboxy-3-hydroxyisothiazol-5-yl)thiomethyl]-1-oxa-1-dethiaceph-3-em-4-oic Acid

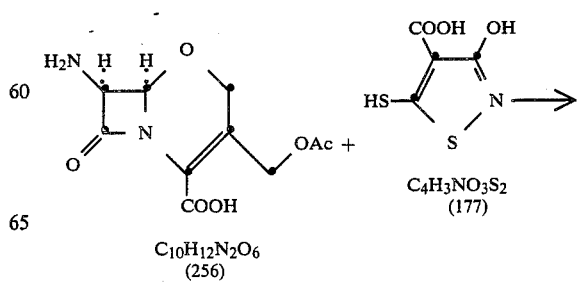

-continued

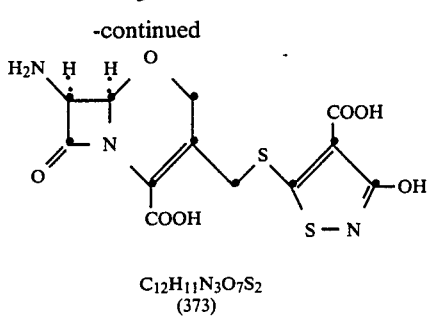

C₁₂H₁₁N₃O₇S₂
(373)

Sodium bicarbonate (9.8 g, 4.25 mol) was added to a suspension of 3-acetoxymethyl 7β-aminooxadethiacephalosporanic acid (7.0 g, 1.0 mol) in water (210 ml) at 25° forming a clear solution to which 3-hydroxy-5-mercaptoisothiazole-4-carboxylic acid (4.8 g, 1.0 mol) was added. The solution was heated to 50° under nitrogen with stirring for 15 hours. The solution was cooled to 20° and slowly acidified with aqueous 2N HCl to pH=3.5 which precipitated the desired product. The solids were filtered off; washed with water (2×25 ml); with acetone (2×25 ml); dried at 50°/0.5 mm; and the titled product obtained as a pale tan powder (4.0 g).

EXAMPLE 5

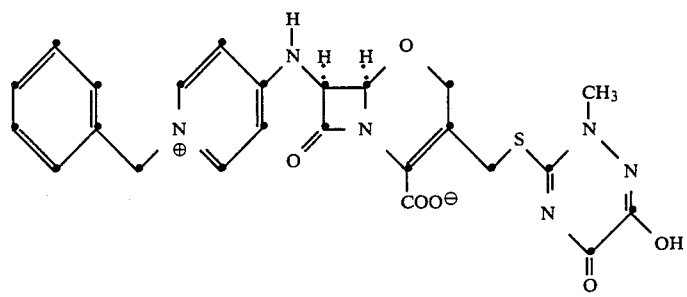

The procedure of Example 1 is repeated using 7β-amino-3-[(2,5-dihydro-6-hydroxy-2-methyl-5-oxo-1,2,4-trioxim-yl)thio methyl]-1-oxa-1-dethiaceph-3-em-4-oic acid as the cephalosporin reactant and 1-benzyl-4-fluoropyridinium bromide as the heterocyclic reactant to produce the compound having the structure indicated hereinabove.

EXAMPLE 6

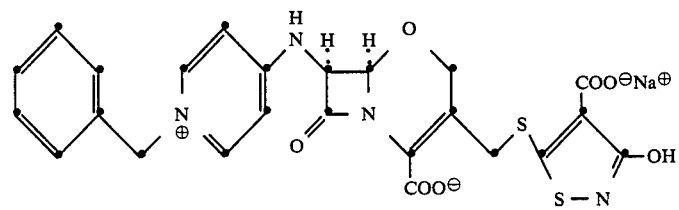

The procedure of Example 1 is repeated using 7β-amino-3-[(4-carboxy-3-hydroxyisothiazol-5-yl)thiomethyl]-1-oxa-1-dethiaceph-3-em-4-oic acid as the cepha-losporin reactant and 1-benzyl-4-fluoropyridinium bromide as the heterocyclic reactant to produce the compound having the structure indicated hereinabove.

What is claimed is:
1. A compound having the structural formula:

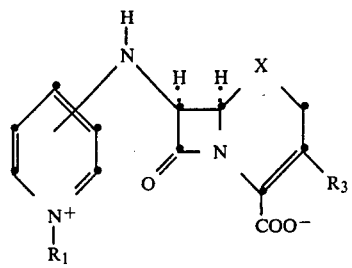

wherein:
$R_1$ is a hydrogen, lower alkyl, phenyl(lower)alkyl,
$R_3$ is a 5- or 6-membered heterocyclic thio methyl substituent selected from:

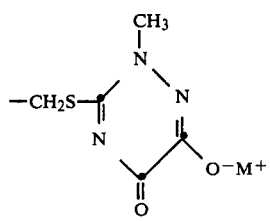

wherein M is an alkali or alkaline earth metallic cation and pharmaceutically accepted salts thereof; and X is sulfur.
2. The compound of claim 1 having the structure:

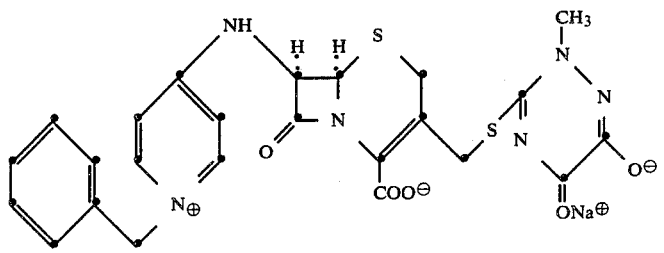
3. An antibacterial pharmaceutical composition comprising a therapeutically effective amount of a compound according to claim 1 and a pharmaceutical carrier therefor.
4. A method of treating a bacterial infection in a living animal comprising the administration of an antibacterially effective amount of a compound according to claim 1.
* * * * *